United States Patent [19]
Eicken et al.

[11] Patent Number: 5,711,942
[45] Date of Patent: Jan. 27, 1998

[54] STORAGE STABLE HAIR CARE EMULSION CONTAINING ONLY NATURAL SUBSTANCES, THEIR MIXTURES AND/OR THEIR REACTION PRODUCTS

[75] Inventors: Ulrich Eicken, Fribourg, Switzerland; Thomas Stiehm, Bielefeld, Germany

[73] Assignee: Wella Aktiengesellschaft, Darmstadt, Germany

[21] Appl. No.: 739,164

[22] Filed: Oct. 30, 1996

[30] Foreign Application Priority Data

Dec. 20, 1995 [DE] Germany ............... 195 47 679.4

[51] Int. Cl.[6] .................................................. A61K 7/035
[52] U.S. Cl. .................... 424/70.1; 424/69; 424/195.11
[58] Field of Search ................. 424/69, 70.1, 195.11

[56] References Cited

U.S. PATENT DOCUMENTS

| | | | |
|---|---|---|---|
| 4,014,995 | 3/1977 | Juliano et al. | 424/168 |
| 5,589,177 | 12/1996 | Herb et al. | 424/401 |

*Primary Examiner*—Terressa Mosley
*Attorney, Agent, or Firm*—Michael J. Striker

[57] ABSTRACT

The hair care emulsion of the invention contains from 0.5 to 5 percent by weight of a monoglyceride of a saturated or unsaturated $C_6$- to $C_{22}$-fatty acid, a polyglycerylmonofattyacid ester of a saturated or unsaturated $C_6$- to $C_{22}$-fatty acid having from 2 to 10 glyceryl groups, a polyglycerylpolyfattyacid ester of a saturated or unsaturated $C_6$- to $C_{22}$-fatty acid having from 2 to 10 glyceryl groups and/or an ester of monosaccharide or disaccharide with a saturated or unsaturated $C_6$- to $C_{22}$-fatty acid; from 0.5 to 5 percent by weight of trimethylglycine and/or panthenol and from 0.5 to 8 percent by weight of one or more saturated or unsaturated $C_6$- to $C_{22}$-fatty acid. The composition according to the invention is free of any surfactant compounds in addition to the above-mentioned ester compounds. The composition according to the invention contains only natural substances, mixtures of them and/or their reaction products and provides hair treated with it with an improved wet and dry combability, and with a pleasant touch and cared-for appearance.

8 Claims, No Drawings

STORAGE STABLE HAIR CARE EMULSION CONTAINING ONLY NATURAL SUBSTANCES, THEIR MIXTURES AND/OR THEIR REACTION PRODUCTS

BACKGROUND OF THE INVENTION

The subject matter of the instant invention is a hair care emulsion which comprises a combination of trimethylglycine and/or panthenol, at least one $C_6$- to $C_{22}$-fatty acid and at least one monoglyceride of a saturated or unsaturated $C_6$- to $C_{22}$-fatty acid or a polyglycerylmono- or polyfatty acid ester of a $C_6$- to $C_{22}$-fatty acid with 2 to 10 glyceryl groups or an ester of a mono- or disaccharide with a saturated or unsaturated $C_6$- to $C_{22}$-fatty acid. The composition of the invention contains no additional surfactant besides the above-named fatty acid esters.

The hair structure is damaged by frequent bleaching, permanent wave treatments and dyeing, but also by frequent washing of hair with oil- or fat-removing surfactant compounds. The hair becomes brittle and looses its luster. The hair further becomes electrostatically charged on combing, and the roughened hair surface causes matting and knotting of the hair. Thus combing of the hair becomes difficult.

Hair care compositions with combability improving action and care effects have achieved a considerable importance. This type of composition frequently, for example, in the form of a clear hair care rinse or also of an emulsion, as a so-called cream-rinse, are distributed on the still wet hair after a hair wash, allowed to act for a few minutes to an hour and then washed or rinsed out of the hair.

Primarily synthetic materials, such as cationic surfactants, cationic polymers and fatty alcohols, are used as effective ingredients for improvement of the hair structure.

SUMMARY OF THE INVENTION

It is an object of the present invention to provide a hair care composition, which exclusively contains natural substances, which means substances of animal, vegetable or mineral origin, mixtures of them and their reaction products, which is stable during storage and which provides wet and dry combability and a pleasant feel and cared for appearance to the hair.

The term "natural substances" according to the invention includes only substances, which can be obtained or further processed from naturally occurring materials by physical means including extraction with water, ethanol, glycerin and carbon dioxide or by enzymatic or micro-biological methods.

According to the invention, the hair care emulsion comprises a combination of a) 0.5 to 5 percent by weight of at least one monoglyceride of a saturated or unsaturated $C_6$- to $C_{22}$-fatty acid, a polyglycerylmonofatty acid ester or polygylcerylpolyfatty acid ester of a saturated or unsaturated $C_6$- to $C_{22}$-fatty acid with 2 to 10 glyceryl groups and/or an ester of a monosaccharide or a disaccharide with a saturated or unsaturated $C_6$- to $C_{22}$- fatty acid, b) 0.5 to 5 percent by weight trimethylglycine and/or panthenol, and c) 0.5 to 8 percent by weight of at least one saturated or unsaturated $C_6$- to $C_{22}$-fatty acid. The hair care composition according to the invention is also free of any additional surfactant besides those included in ingredient a).

This hair care composition according to the invention achieves the objects of the invention in an outstanding manner.

The composition according to the invention preferably contains from 1 to 2.5 percent by weight of the above ingredient a). The esters of saturated $C_{10}$- to $C_{18}$-fatty acids and of oleic acid, also the monoglyceride of the saturated $C_{10}$- to $C_{18}$-fatty acids or oleic acid, the polyglycerylmono- or -polyfatty acid esters of saturated $C_{10}$- to $C_{18}$-fatty acids or oleic acid with 2 to 10 glyceryl groups and the saturated $C_{10}$- to $C_{18}$-fatty acid esters or oleic acid esters of monosaccharides and disaccharides are suitable as the fatty acid esters of ingredient a).

The $C_6$- to $C_{22}$-fatty acid esters of saccharose, glucose or fructose can be used as the saturated or unsaturated fatty acid esters of monosaccharides or disaccharides.

Glycerin monolaurate, which is marketed under the tradename, Monomuls® 90-L-12, and the glycerin monooleate, which is marketed under the tradename, Monomuls® 90-O-18, of Henkel KGaA, Dusseldorf, Germany, for example are suitable as the monoglyceride of the $C_6$- to $C_{22}$-fatty acids of ingredient a).

Polyglycerylmono- or -polyfatty acid esters suitable as ingredient a) above are, for example, the following ester compounds of Nikkol Chem. Co. Ltd., Japan listed with their tradenames in parentheses: diglycerylmonostearate (Nikkol® DGMS), diglycerylmonooleate(Nikkol® DGMO-C,Nikkol® DGMO-90), diglyceryldioleate (Nikkol® DGDO), diglycerylmonoisostearate (Nikkol® DGMIS), tetraglycerylmonostearate (Tetraglyn® 1-S), tetraglycerylmonooleate (Tetraglyn® 1-O), tetraglyceryltristearate (Tetraglyn® 3-S), tetraglycerylpentastearate (Tetraglyn® 5-S), tetraglycerylpentaoleate (Tetraglyn® 5-O), hexaglycerylmonolaurate (Hexaglyn® 1-L), hexaglycerylmonomyristate (Hexaglyn® 1-M) , hexaglycerylmonostearate (Hexaglyn® 1-S) , hexaglycerylmonooleate (Hexaglyn® 1-O) , hexaglyceryltristearate (Hexaglyn® 3-S), hexaglycerylpentastearate (Hexaglyn® 5-S ) , hexaglycerylpentaoleate (Hexaglyn® 5-O), hexaglycerylpolyricinolate (Hexaglyn® PR-15), decaglycerylmonolaurate (Decaglyn® 1-L), decaglycerylmonomyristate (Decaglyn® 1-M) and decaglycerylmonostearate (Decaglyn® 1-S); triglyceryldioleate sold by BASF, Ludwigshafen, Germany under the tradename Cremophor® GO-32, and triglycerylstearate sold under the tradename of Polyaldo® TGMS of Lonza Inc, USA and decaglycerylmonostearate sold in the form of a 40 percent solution under the tradename Polyaldo® 10-1-S of Lonza Inc, USA.

An ester of coconut oil fatty acids (saturated $C_{12}$- to $C_{14}$-fatty acids) and saccharose, which, for example, is marketed under the tradename Ryoto® LWA 1570 in the form of a 40 percent aqueous-ethanolic Solution by Ryoto Co. Ltd., Japan, is particularly preferred as ingredient a).

The hair care emulsion according to the invention particularly preferably contains from 1 to 3 percent by weight of a mixture of panthenol and trimethylglycine (which is also designated as betaine) as ingredient b).

The ingredient c) is preferably present in the composition according to the present invention in an amount of from 1.5 to 3 percent by weight. The composition according to the invention contains preferably at least one saturated $C_{10}$- to $C_{18}$- fatty acid and/or oleic acid. Suitable saturated fatty acids for use as ingredient c) are, e.g., myristic acid or coconut oil fatty acids.

In a special embodiment of the invention in addition to the ingredients a), b) and c) the composition contains from 0.005 to 1 percent by weight, advantageously 0.1 to 0.3 percent by weight lecithin and/or 0.1 to 4 percent by weight of cosmetically compatible natural oils and/or 0.1 to 4 percent by weight cosmetically compatible natural waxes.

Lecithin suitable for use in the composition according to the invention includes Soja lecithin, which, e.g., is sold by Laserson S. A., France, under the tradename Mactan® P-97, and lecithin from eggs sold by Lucas Meyer, Hamburg, Germany, under the tradename Emulmetik® 970.

Cosmetically compatible natural oils suitable for use in the composition according to the invention include, e.g., wheat germ oil, sunflower oil, avocado oil, jojoba oil, babassu oil and macademia oil. Suitable cosmetically compatible natural waxes include, e.g., bees wax, apple wax, wool wax, flax wax and Shea butter.

The hair care emulsion according to the invention can also include all those cosmetic additive ingredients, which are conventionally used in hair care compositions and which are natural substances within the above-stated definition, especially natural organic or inorganic thickening agents, such as xanthan gum or a mixture of sodium alginate, glucose, guar gum and carageen, which is sold under the tradename Cremodan® DC by Danisco Århus, Denmark, in amounts from 0.5 to 10 percent by weight; organic acids, such as citric acid or lactic acid; preservative agents such as sorbic acid, salicylic acid, benzoic acid, propionic acid, 4-hydroxybenzoic acid and formic acid and their salts, 2-phenoxyethanol and benzyl alcohol, in amounts of 0.05 to 1 percent by weight; antioxidants, such as oxidation preventing extracts, such as Rosmarin extract, sold, for example, under the tradename Stabiliton® OS by RAPS, in an amount of 0.1 to 1.5 percent by weight; moisturizing agents, such as glycerin, saccharides and hyaluronic acid, in amounts of from 0.1 to 2 percent by weight; hair care materials, such as lanolin, cholesterol, protein hydrolyzates, such as keratin hydrolyzates and pantothenic acids, in amounts of from 0.1 to 10 percent by weight and natural perfume oils, in so far as these additives appear to be useful and suitable and are compatible with the ingredients of the composition according to the invention.

The composition according to the invention contains no additional nonionic surfactants in addition to those in ingredient a) and is free of amphoteric, anionic and cationic surfactant.

The composition according to the invention is in the form of an oil-in-water emulsion and has a water content 60 to 98 percent by weight, advantageous from 80 to 95 percent by weight and a pH of from 2 to 7, advantageously from 3 to 5.

In a special embodiment according to the invention the hair care emulsion according to the invention contains from 0.05 to 2.0 percent by weight of at least one natural dye compounds, such as vegetable dyes, such as henna or reng or anthocyanide dye compounds.

The hair care emulsion according to the present invention is, usually after washing the hair, distributed in hand-towel dried hair according to the amount of the hair in an amount of 5 to 20 g. After an acting time of 1 to 15 minutes the hair is rinsed with water and then dried.

The acting time of the composition according to the invention depends within predetermined time limits on the purpose of its application. If it is a matter of a rinse the acting time amounts to from 1 to 5 minutes, while the acting time amounts to 3 to 15 minutes for hair care.

The following examples should clearly illustrate the subject matter of the invention without limiting the appended claims.

EXAMPLES

Example 1: Natural Cosmetic Hair Rinse 2.70 g coconut oil fatty acid saccharoester (Ryoto® LWA 1570 of Ryoto Co. Ltd.)
1.00 g panthenol
1.00 g trimethylglycine
1.50 g myristic acid
0.20 g Soja lecithin (Mactan® P-97)
3.50 g wheat germ oil
1.50 g bees wax
0.20 g benzoic acid
0.50 g natural perfume oil
0.50 g xanthan gum
87.40 g water 100.00 g Example 2: Hair Care Emulsion 1.00 g saccharose laurate
2.00 g panthenol
1.50 g myristic acid
4.00 g wheat germ oil
1.00 g apple wax
0.10 g Soja wax lecithin
0.15 g sodium benzoate
0.23 g sodium formate
0.50 g natural perfume oil
0.50 g xanthan gum
0.85 g citric acid
0.10 g ethanol
88.07 g water 100.00 g Example 3: Hair Care Emulsion 1.00 g saccharose laurate
2.00 g trimethylglycine
1.50 g myristic acid
4.00 g Wheat germ oil
1.00 g apple wax
0.10 g Soja wax lecithin
0.15 g sodium benzoate
0.23 g sodium formate
0.50 g natural perfume oil
0.50 g xanthan gum
0.85 g citric acid
0.10 g ethanol
88.07 g water 100.00 g Example 4: Hair Care Emulsion 1.002 g saccharose laurate
2.000 g panthenol
2.000 g trimethylglycine
0.500 g palmitic acid
0.500 g stearic acid
3.000 g almond oil
1.000 g bees wax
0.150 g sodium benzoate
0.230 g sodium formate
0.500 g natural perfume oil
0.500 g xanthan gum
0.300 g citric acid
0.100 g ethanol
88.218 g water 100.00 g Example 5: Hair Care Emulsion 0.100 g triglycerylmonostearate
0.873 g decaglycerylmonostearate
2.000 g D-panthenol
2.000 g trimethylglycine
1.500 g palmitic acid
1.500 g stearic acid
2.000 g almond oil
1.000 g bees wax
0.500 g tea tree oil

```
0.500 g  natural perfume oil
0.200 g  rosmarin extract
0.500 g  xanthan gum
0.027 g  polyglycerin
0.300 g  citric acid
87.000 g water 100.00 g
```

Example 6: Hair Care Emulsion

```
0.100 g  triglycerylmonostearate
0.873 g  decaglycerylmonostearate
2.000 g  D-panthenol
2.000 g  trimethylglycine
1.500 g  palmitic acid
1.500 g  stearic acid
2.000 g  almond oil
1.000 g  bees wax
0.150 g  sodium benozoate
0.230 g  sodium formate
0.500 g  natural perfume oil
0.300 g  citric acid
0.500 g  xanthan gum
0.027 g  polyglycerin
87.320 g water 100.00 g
```

All percentages indicated in the foregoing disclosure, unless otherwise indicated, are in percentages by weight.

We claim:

1. A hair care emulsion consisting only of at least one of natural substances, mixtures of said natural substances and reaction products of said natural substances, and said hair care emulsion containing from 0.5 to 5 percent by weight of at least one ester compound selected from the group consisting of monoglycerides of saturated or unsaturated $C_6$- to $C_{22}$-fatty acids, polyglycerylmonofatty acid esters of saturated or unsaturated $C_6$- to $C_{22}$-fatty acids having from 2 to 10 glyceryl groups, polyglycerylpolyfatty acid esters of saturated or unsaturated $C_6$- to $C_{22}$-fatty acids having from 2 to 10 glyceryl groups, esters of monosaccharides with saturated or unsaturated $C_6$- to $C_{22}$-fatty acids and esters of disaccharides with saturated or unsaturated $C_6$- to $C_{22}$-fatty acids;

from 0.5 to 5 percent by weight of at least one member selected from the group consisting of trimethylglycine and panthenol, from 0.5 to 8 percent by weight of at least one saturated or unsaturated $C_6$- to $C_{22}$-fatty acid;

and free of any surfactant compounds in addition to those included in said at least one ester compound.

2. The hair care emulsion as defined in claim 1, further comprising from 0.005 to 1 percent by weight lecithin.

3. The hair care emulsion as defined in claim 1, further comprising from 0.1 to 4 percent by weight of at least one cosmetically compatible natural oil.

4. The hair care emulsion as defined in claim 3, wherein said at least one cosmetically compatible natural oil is selected from the group consisting of wheat germ oil, sunflower oil, avocado oil, jojoba oil, babassu oil and macadamia oil.

5. The hair care emulsion as defined in claim 1, further comprising from 0.1 to 4 percent by weight of at least one cosmetically compatible natural wax.

6. The hair care emulsion as defined in claim 5, wherein said at least one cosmetically compatible natural wax is selected from the group consisting of bees wax, apple wax, wool wax, flax wax and Shea butter.

7. The hair care emulsion as defined in claim 1, wherein said at least one ester compound is selected from the group consisting of monoglycerides of saturated $C_{10}$- to $C_{18}$-fatty acids, polyglycerylmonofatty acid esters of saturated $C_{10}$- to $C_{18}$-fatty acids having from 2 to 10 glyceryl groups, polyglycerylpolyfatty acid esters of saturated $C_{10}$- to $C_{18}$-fatty acids having from 2 to 10 glyceryl groups, monosaccharides of saturated $C_{10}$- to $C_{18}$-fatty acids, disaccharides of saturated $C_{10}$- to $C_{18}$-fatty acids, monoglycerides of oleic acid, polyglycerylmonofatty acid esters of oleic acid having from 2 to 10 glyceryl groups, polyglycerylpolyfatty acid esters of oleic acid having from 2 to 10 glyceryl groups, monosaccharides of oleic acid, disaccharides of oleic acid and mixtures thereof.

8. The hair care emulsion as defined in claim 1, wherein said at least one ester compound consists of an ester of a saturated $C_{12}$- to $C_{14}$-fatty acid with saccharose.

* * * * *